(12) United States Patent
Schmalhurst et al.

(10) Patent No.: US 8,380,302 B2
(45) Date of Patent: Feb. 19, 2013

(54) IMPLANTABLE MEDICAL DEVICE INCLUDING EDDY CURRENT REDUCING CAPACITOR

(75) Inventors: Lisa B. Schmalhurst, Bellevue, WA (US); Gregory J. Sherwood, Shoreview, MN (US); Masoud Ameri, Maple Plain, MN (US); Yingbo Li, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 176 days.

(21) Appl. No.: 12/980,891

(22) Filed: Dec. 29, 2010

(65) Prior Publication Data

US 2011/0160826 A1 Jun. 30, 2011

Related U.S. Application Data

(60) Provisional application No. 61/291,591, filed on Dec. 31, 2009.

(51) Int. Cl.
*A61N 1/00* (2006.01)

(52) U.S. Cl. .......................................................... 607/2

(58) Field of Classification Search ................ 607/2, 36; 600/377; 174/359; 219/535; 257/531; 324/318; 333/172; 361/302, 306.3, 503
See application file for complete search history.

(56) References Cited

U.S. PATENT DOCUMENTS

| 4,800,883 | A | | 1/1989 | Winstrom |
| 4,821,723 | A | | 4/1989 | Baker, Jr. et al. |
| 5,099,387 | A | * | 3/1992 | Kato et al. ................. 361/321.2 |
| 7,006,347 | B1 | * | 2/2006 | Kroll et al. .................... 361/503 |
| 7,765,005 | B2 | | 7/2010 | Stevenson |
| 7,769,457 | B2 | | 8/2010 | Fonte |
| 2004/0199069 | A1 | | 10/2004 | Connelly et al. |
| 2005/0264979 | A1 | | 12/2005 | Breyen et al. |
| 2006/0023396 | A1 | * | 2/2006 | Sherwood ..................... 361/302 |
| 2007/0106332 | A1 | | 5/2007 | Denker et al. |
| 2009/0243756 | A1 | * | 10/2009 | Stevenson et al. ............ 333/172 |
| 2010/0174349 | A1 | | 7/2010 | Stevenson et al. |

FOREIGN PATENT DOCUMENTS

| EP | 1424098 A1 | 6/2004 |
| WO | WO-97/41923 A1 | 11/1997 |

OTHER PUBLICATIONS

"International Application Serial No. PCT/US2010/062348, International Search Report mailed Apr. 4, 2011", 4 pgs.
"International Application Serial No. PCT/US2010/062348, Written Opinion mailed Apr. 4, 2011", 7 pgs.
"International Application Serial No. PCT/US2010/062348, International Preliminary Report on Patentability mailed Jul. 12, 2012", 8 pgs.

* cited by examiner

*Primary Examiner* — George Manuel
*Assistant Examiner* — Robert N Wieland
(74) *Attorney, Agent, or Firm* — Schwegman Lundberg & Woessner, P.A.

(57) ABSTRACT

An implantable device, such as a pacer, defibrillator, or other cardiac rhythm management device, can include one or more MRI Safe components. In an example, the implantable device includes a capacitor including a first electrode including a first slot extending from a perimeter of the first electrode to an interior of the first electrode. A second electrode is separated from the first electrode by a first distance. The second electrode includes a second slot extending from a perimeter of the second electrode to an interior of the second electrode. The first and second slots are configured to at least partially segment surface areas of the first and second electrodes, respectively, to reduce a radial current loop size in each of the first and second electrodes.

19 Claims, 5 Drawing Sheets

US 8,380,302 B2

IMPLANTABLE MEDICAL DEVICE INCLUDING EDDY CURRENT REDUCING CAPACITOR

CROSS-REFERENCE TO RELATED APPLICATIONS

This application claims the benefit of U.S. Provisional Application No. 61/291,591, filed on Dec. 31, 2009, under 35 U.S.C. §119(e), which is incorporated herein by reference in its entirety.

BACKGROUND

Implantable medical devices (IMDs) can perform a variety of diagnostic or therapeutic functions. For example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), or cardiac resynchronization therapy (CRT) devices, among others. Nuclear magnetic resonance imaging (MRI), is a medical imaging technique that can be used to visualize internal structure of the body. MRI is an increasingly common diagnostic tool, but can pose risks to a person with an IMD, such as a patient undergoing an MRI scan or a person nearby MRI equipment, or to people having a conductive implant.

In a MR field, an item, such as an IMD, can be referred to as "MR Safe" if the item poses no known hazard in all MRI environments. In an example, MR Safe items can include non-conducting, non-metallic, non-magnetic materials, such as glass, porcelain, a non-conductive polymer, etc. An item can be referred to as "MR Conditional" in the MR field if the item has been demonstrated to pose no known hazards in a specified MRI environment with specified conditions of use (e.g., static magnetic field strength, spatial gradient, time-varying magnetic fields, RF fields, etc.). In certain examples, MR Conditional items can be labeled with testing results sufficient to characterize item behavior in a specified MRI environment. Testing can include, among other things, magnetically induced displacement or torque, heating, induced current or voltage, or one or more other factors. An item known to pose hazards in all MRI environments, such as a ferromagnetic scissors, can be referred to as "MR Unsafe."

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
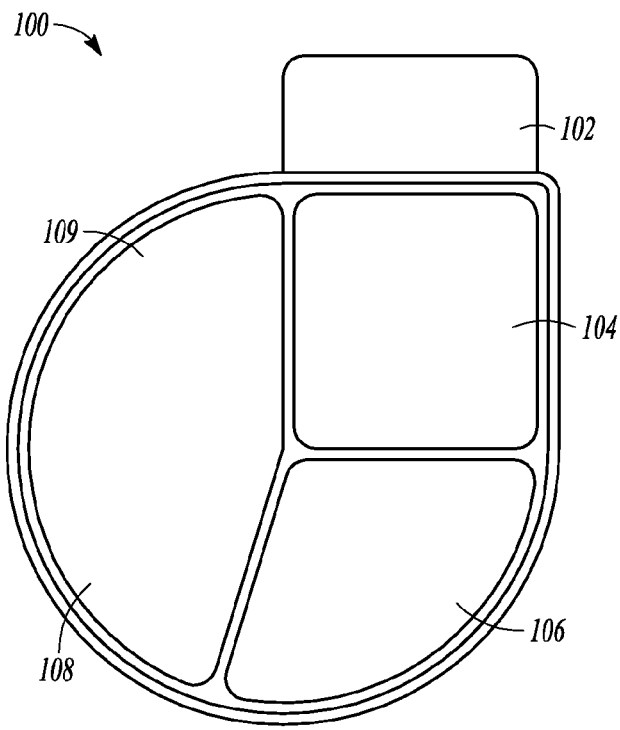
FIG. 1 illustrates a cut-away view of an IMD showing basic components of the IMD.

Nuclear magnetic resonance (NMR) devices (e.g., an MRI scanner, an NMR spectrometer, or other NMR device) can produce both static and time-varying magnetic fields. For example, an MRI scanner can provide a strong static magnetic field, $B_0$, such as to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered such as to alter the alignment of specified nuclei (e.g., within a particular volume or plane to be imaged within the subject). The power, phase, and range of frequencies of the one or more RF excitation pulses can be selected, such as depending on the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during MR, such as to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization" of signals detected by the RF receiver, such as by using frequency discrimination. Using a gradient field allows a volume or plane to be imaged more efficiently. In a gradient field example, signals received from relaxing nuclei can include energy in respective unique frequency ranges corresponding to the respective locations of the nuclei.

Active MRI equipment can induce unwanted torques, forces, or heating in an IMD or other conductive implant, or can interfere with operation of the IMD. In certain examples, the interference can include disruption in sensing by the IMD, interference in communication between the IMD and other implants or external modules during MRI operation, or disruption in monitoring or therapeutic function of the IMD.

During an MRI scan, the one or more RF excitation pulses can include energy delivered at frequencies from less than 10 MHz to more than 100 MHz, such as corresponding to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, such as including individual time-varying gradient fields provided in each of the axes to provide imaging in multiple dimensions.

In an example, the static field, $B_0$, can induce unwanted forces or torques on ferromagnetic materials, such as steel or nickel. The forces or torques can occur even when the materials are not directly within the "bore" of the MRI equipment—because significant fields can exist near the MRI equipment. Moreover, if an electric current is switched on or off in the presence of the $B_0$ field, a significant torque or force can be suddenly imposed in the plane of the circulation of the current, even though the $B_0$ field itself is static. The induced force or torque can be minimal for small currents, but the torque can be significant for larger currents, such as those delivered during defibrillation shock therapy. For example, assuming the circulating current is circulating in a plane normal (e.g., perpendicular) to the static field, the torque can be proportional to the magnitude of the $B_0$ field, multiplied by the surface area of the current loop, multiplied by the current.

Time-varying fields, such as the gradient field or the field associated with the RF excitation pulse, can present different risks than the static field, $B_0$. For example, the behavior of a wire loop in the presence of a time-varying magnetic field can be described using Faraday's law, which can be represented by $$\varepsilon = -\frac{d\Phi_{B_1}}{dt},$$

in which $\varepsilon$ can represent the electromotive force (e.g., in volts), such as developed by a time-varying magnetic flux. The magnetic flux can be represented as $$\Phi_{B1} = \iint_S B_1 \cdot dS,$$

in which $B_1$ can represent an instantaneous magnetic flux density vector (e.g., in Webers per square meter, or Tesla). If $B_1$ is relatively uniform over the surface S, then the magnetic flux can be approximately $\Phi_{B1}=|B_1||A|$, where A can represent the area of the surface S. Operating MRI equipment can produce a time-varying gradient field having a slew rates in excess of 100 Tesla per second (T/s). The slew rate can be similar to a "slope" of the gradient field, and is thus similar to $$\frac{d\Phi_{B_1}}{dt}.$$

The electromotive force (EMF) of Faraday's law can cause an unwanted heating effect in a conductor—regardless of whether the conductor is ferromagnetic. EMF can induce current flow in a conductor (e.g., a housing of an IMD, one or more other conductive regions within an IMD, or one or more other conductive implants). The induced current can dissipate energy and can oppose the direction of the change of the externally applied field (e.g., given by Lenz's law). The induced current tends to curl away from its initial direction, forming an "eddy current" over the surface of the conductor, such as due to Lorentz forces acting upon electrons moving through the conductor. Because non-ideal conductors have a finite resistivity, the flow of induced current through the conductor can generate heat. The induced heat can cause a significant temperature rise in or near the conductor over the duration of the scan. The eddy current power deposition can be proportional to the square of both the peak flux density and the frequency of the excitation.

Generally, induced currents, such as induced by the RF magnetic excitation pulse, can concentrate near the surface of a conductor, a phenomenon that can be referred to as the skin effect. The skin effect can limit both the magnitude and depth of the induced current, thus reducing power dissipation. However, the gradient field can include energy at a much lower frequency than the RF magnetic excitation field, which can more easily penetrate through the housing of the IMD. Unlike the field from the RF excitation pulse, the gradient field can more easily induce bulk eddy currents in one or more conductors within the IMD housing, such as within one or more circuits, capacitors, batteries, or other conductors.

Aside from heating, the MRI gradient induced EMF can create, among other things, non-physiologic voltages that can cause erroneous sensing of cardiac electrical activity, or the EMF can create a voltage sufficient to depolarize cardiac tissue or render the cardiac tissue refractory, possibly affecting pacing therapy. In an illustrative example, an IMD can be connected to one or more leads, such as one or more subcutaneous or intravascular leads positioned to monitor the patient, or to provide one or more therapies to the patient. In this illustrative example, a surface area of a "circuit" including the lead, the housing of the IMD, and a path through at least partially conductive body tissue between an electrode on the lead and the IMD housing can be more than 300 square centimeters, or more than 0.03 square meters. Thus, using Faraday's law, the electromotive force (EMF) developed through the body tissue between the electrode (e.g., a distal tip or ring electrode) of the lead and the housing of the IMD can be more than 0.03 square meters times 100 t/s, or more than 3 volts.

The present inventors have recognized, among other things, that it is desirable for IMDs to include increased safety within an MRI environment. For instance, the present inventors have recognized that it is desirable for IMDs to include a decreased response to the magnetic fields present within or otherwise proximate an MRI device. Such responses include, but are not limited to, heating, vibration or other induced movement, induced voltages, and the like. In some examples, the present inventors have recognized that it is desirable to reduce the magnetic field response of capacitors present in IMDs.

Referring to FIG. 1, an example of an IMD 100 is shown. The IMD 100, in an example, includes a header 102 for attaching a component, such as a lead, to the IMD. In an example, the IMD 100 includes an electronic module 104 including electronics of the IMD 100 associated with the operation and functioning of the IMD 100 within a patient. In some examples, the IMD 100 includes a cell or battery 106. In some further examples, the IMD 100 includes a capacitor 108. In various examples, one or more of the components 102, 104, 106, 108 or other components of IMDs which are not shown in FIG. 1, such as leads, for instance, can include decreased response to magnetic fields for increased safety within the MRI environment. As such, the description herein, although describing primarily decreased MR response in capacitors, can be applied to any components or combinations of components of an IMD, including also metal or otherwise conductive enclosures of the components of the IMD or of the IMD itself. Examples of IMDs that can include metal enclosures and/or internal large surface area components include but are not limited to, cardiac pacemakers; automatic implantable cardioverter-defibrillators (ICDs); cardiac resynchronization therapy and defibrillator (CRT-D) devices; neuromodulators including deep brain stimulators (DBS), various pain control devices, and lead systems for stimulation of the spinal cord, muscles, and other nerves of the body (such as, for instance, the vagal nerve); implantable diagnostic devices for monitoring cardiac function; cochlear implants; and drug pumps for administering periodic or demand based pharmacological therapy.

In various examples, the capacitor 108 includes an enclosure 109. In some examples, the capacitor 108 can include one or more anode layers, one or more cathode layers, and one or more separators, which are each in stacked alignment with one another, within the enclosure 109. Some examples include layers with connection members used for interconnecting to other layers. In various examples, a connection member extends away from the stacked layers, enabling interconnection among capacitor layers. For example, a number of anode connection members can extend away from the anode layers of the capacitor 108 for interconnection of the anode layers. In some examples, connection members can be used for the cathode layers. It is noted that, although portions of the description below focus on only one or two electrodes, the description of those sections can be applied to capacitors including more than one anode layer and/or more than one cathode layer.

In various examples, the capacitor 108 can include an aluminum electrolytic (AE) capacitor. In some examples, the AE capacitor includes at least one anode layer and at least one cathode layer, with the anode and cathode layers each including aluminum. In an example, the AE capacitor includes one or more anode layers including aluminum oxide on an aluminum substrate. In a further example, the aluminum substrate is etched. In an example, the AE capacitor includes one or more cathode layers including titanium on an aluminum substrate. In further examples, an electrolyte can be disposed between each of the layers of the AE capacitor. In further examples, a separator such as capacitor paper can be disposed between layers of the AE capacitor. Although materials of electrodes or other capacitor components may not be specified in the examples described below, it is noted that at least some of the examples below can be used with respect to AE capacitors, as well as with other types of capacitors and other IMD components.

Figure 2:
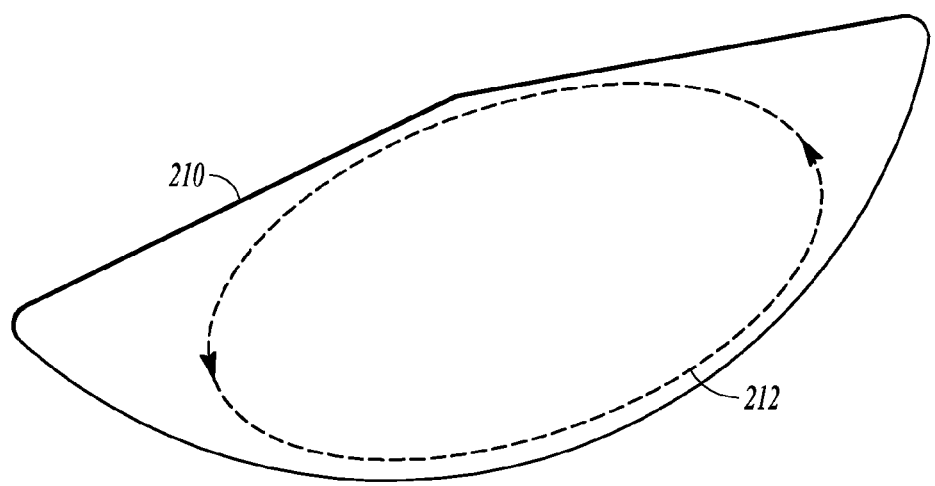
FIG. 2 illustrates an example of an un-segmented electrode.

Referring to FIG. 2, in various examples, a capacitor (such as the capacitor 108 of the IMD 100 of FIG. 1) can include an electrode 210. An arrow 212 is depicted on the electrode 210 to portray an example radial current or eddy current of the electrode 210, such as could be induced by a gradient field of an MRI device. In an example, an induced eddy current can interact with the static magnetic field and can result in vibration or other movement of the electrode 210 (and, in turn, the capacitor). In another example, the induced eddy current can be dissipated as heat to elevate the temperature of the electrode 210 (and, in turn, the capacitor). For a given time varying gradient field, the induced torque and/or generated heat are functions of the material and the geometry of the electrode 210. For instance, the eddy current induced heating and vibration are generally proportional to the square of the surface area of the conductor, or, in the example of FIG. 2, generally the area encompassed by the induced eddy current shown by arrow 212. Because of the relatively large surface area (and the relatively large loop 212 of the eddy current) of the example electrode 210, a capacitor of an IMD can be a substantial source of heat and/or vibration when placed within an MRI environment. Accordingly, reduction of the loop size of an induced eddy current present in, for instance, an electrode of a capacitor of an IMD, is contemplated herein to reduce heating and/or movement induced in an IMD subjected to an MRI environment.

For instance, in AE capacitor examples, due, at least in part, to the relatively high conductivity of aluminum, an electrode of the AE capacitor can be relatively highly responsive to magnetic fields of an MRI environment, such as the gradient field of an MRI device. Moreover, in some examples, because thin aluminum foils can be used for electrodes of the AE capacitor, the electrodes can have a limited thermal mass, which can contribute to such electrodes heating up relatively quickly. Heating and/or vibration of components of implanted devices can be hazardous to a patient having an implanted device and being subjected to an MRI environment. For instance, heating and/or vibration of components of implanted devices can result in tissue damage to the patient. As such, the present inventors have recognized that it can be desirable to reduce surface areas of one or more components of implantable devices to limit the response (for instance, heating and/or vibration) of such implantable devices to an MRI environment, thereby making the implantable device MRI Safe. In some examples, as described in more detail below, the present inventors have recognized that a component of an implantable device can be segmented to reduce a surface area of the component, thereby decreasing the size of the radial current loop and reducing the response of the component to an MRI environment. Several examples of such segmented components are described below.

Figure 3:
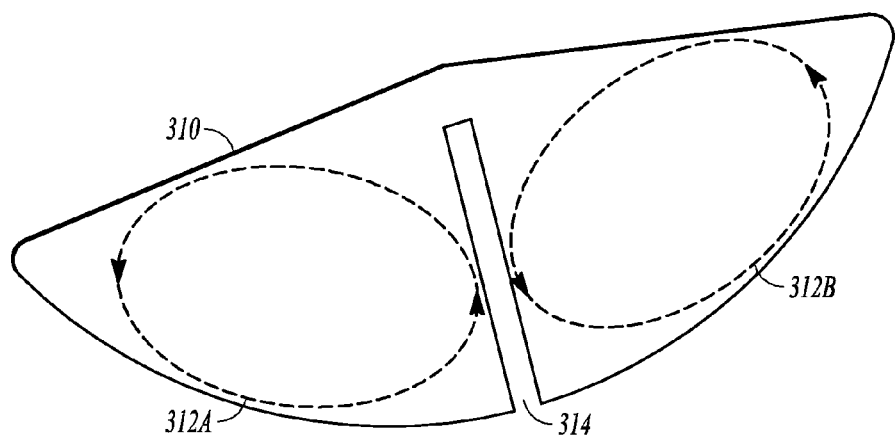
FIG. 3 illustrates an example of a segmented electrode.

Referring to FIG. 3, a segmented electrode 310 of a capacitor (such as, for instance, the capacitor 108 of FIG. 1) in accordance with some examples is shown. In some examples, the electrode 310 includes an opening or slot 314 extending from a perimeter of the electrode 310 to an interior of the electrode 310. In other examples, the electrode can include more than one slot. In the example shown in FIG. 3, the slot 314 provides a break in the surface area of the electrode 310, which can result in smaller radial current loops of eddy currents (relative to the loop size of the eddy current of an unsegmented electrode, such as the example electrode 210 of FIG. 2), as depicted by arrows 312A, 312B. By reducing the loop size of the eddy currents in the electrode 310, in an example, the heating and/or movement induced by an MRI environment can be reduced to a level at which the IMD and/or the capacitor of the IMD are deemed MRI Safe. Because removal of electrode material can generally adversely affect performance and effectiveness of the capacitor, a consideration in segmentation of the electrode 310 is minimal material removal. In an example, by optimizing a pattern of the segmentation of the electrode 310, the performance of the capacitor can be minimally impacted while, at the same time, sufficiently minimizing eddy current loop size to result in an MRI Safe capacitor.

Figure 4:
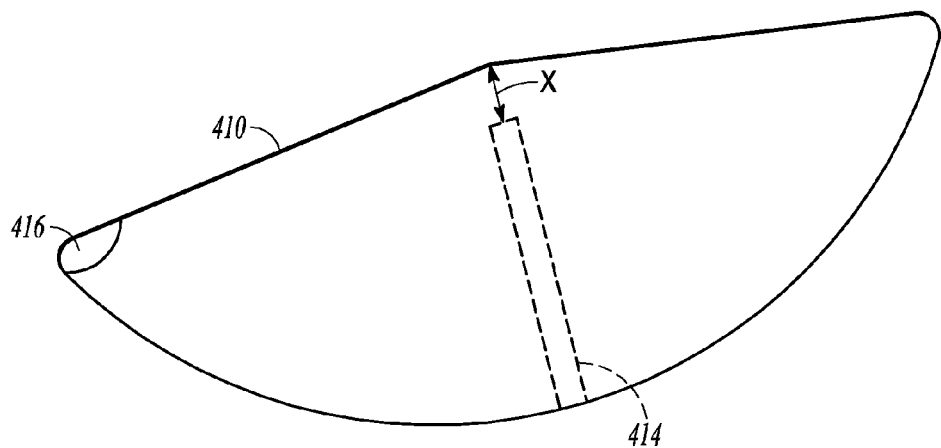
FIG. 4 illustrates an example of an un-segmented electrode including an interconnect area.

Referring to FIG. 4, an example of an unsegmented electrode 410 includes an interconnection area 416. In various examples, the interconnection area 416 can allow for connection of the electrode 410 with one or more similar electrodes of a capacitor. For instance, as described above, two or more anode layers of a capacitor can be connected, and/or two or more cathode layers of a capacitor can be connected. However, in an example, if the electrode 410 of FIG. 4 were to be segmented with an opening or slot 414 (shown in phantom), current during charge and/or discharge of the capacitor would have to flow through a reduced cross section, as illustrated by arrow X in FIG. 4. Such "funneling" of current through the reduced cross section X of the electrode 410, in some examples, can increase equivalent series resistance (ESR) of the capacitor, which can be detrimental to the performance of the capacitor. As such, the present inventors have recognized that it can be desirable to reposition the interconnection area of the electrode.

Figure 5:
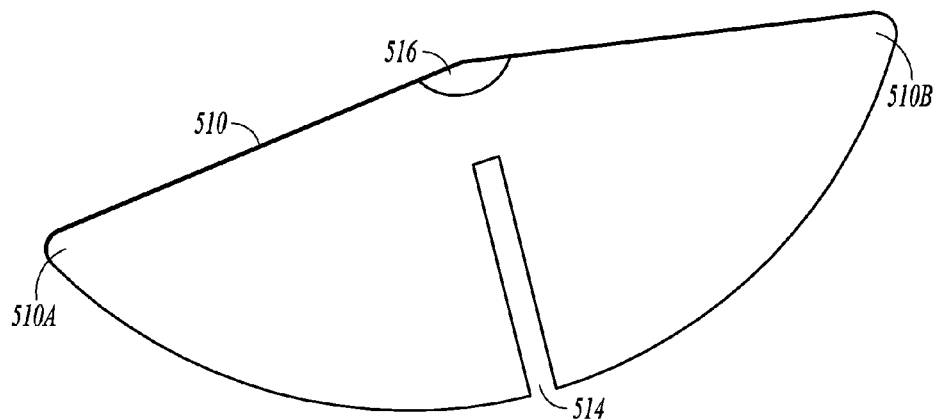
FIG. 5 illustrates an example of a segmented electrode including an interconnect area.

Referring to FIG. 5, in some examples, a segmented electrode 510 includes an opening or slot 514 and an interconnection area 516 repositioned relative to the interconnection area 410 of the example electrode 410 of FIG. 4. In this example, the interconnection area 516 is substantially centrally located between portions 510A, 510B of the electrode 510 along an edge of the electrode 516 and substantially proximate an end of the slot 514 disposed in an interior of the electrode 510. That is, the interconnection area 516 of this example can be located at or near an area of reduced cross section between an interior end of the slot 514 and the edge of the electrode 510 so that current can flow between the interconnection area 516 and each of the portions 510A, 510B of the electrode 510 with little or at least decreased "funneling" of current, as can be present in the configuration of the example electrode 410 described above. In this way, increases in ESR and other detrimental performance effects of the capacitor due to the reduced cross section of the electrode 510 can be reduced.

Figure 6:
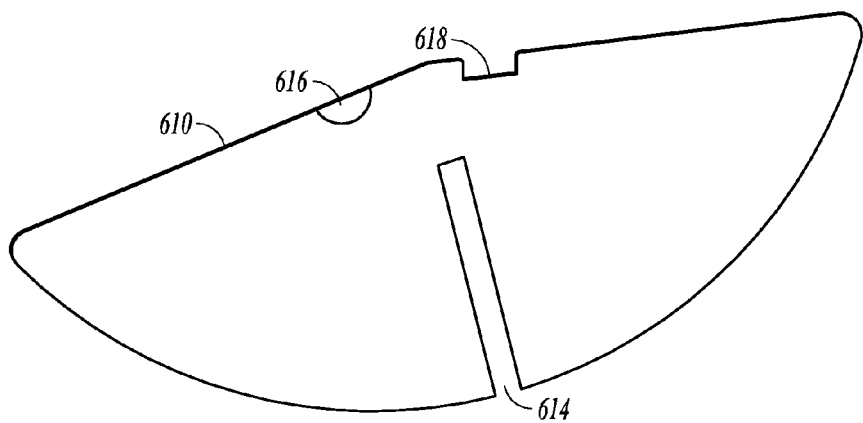
FIG. 6 illustrates an example of a segmented electrode including an interconnect area.
Figure 7:
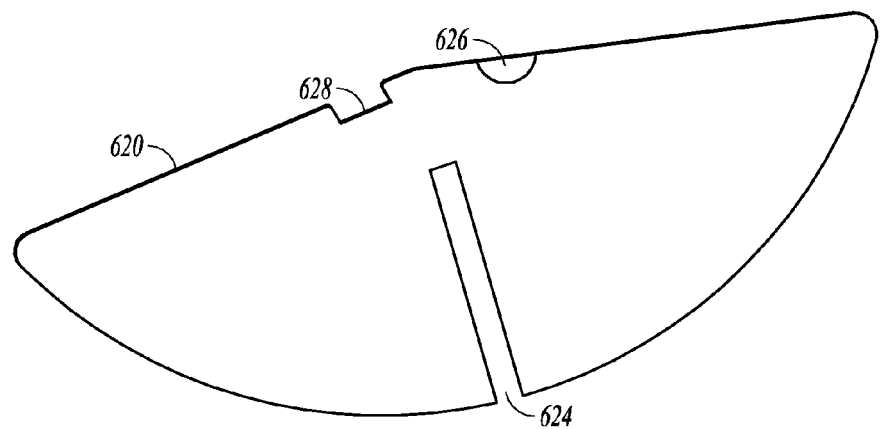
FIG. 7 illustrates an example of a segmented electrode including an interconnect area.
Figure 8:
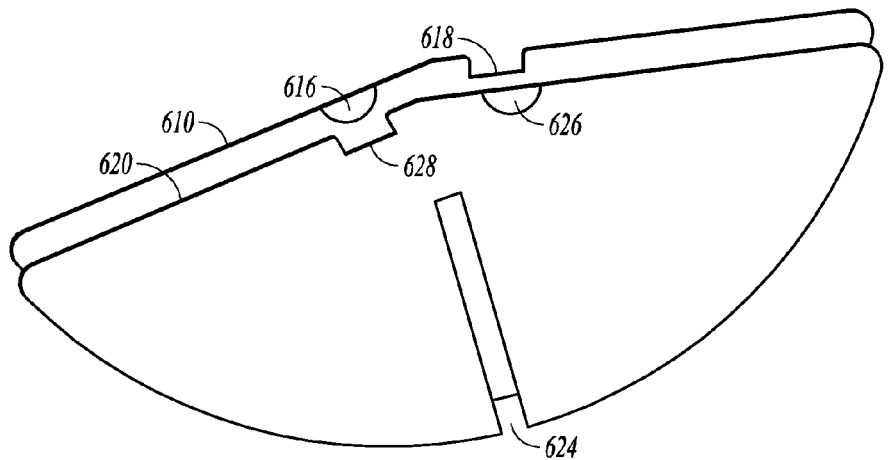
FIG. 8 illustrates an example of segmented electrodes including interconnect areas, the segmented electrodes including substantially aligned segmentations.

Referring to FIGS. 6-8, in some examples, a segmented first electrode 610 includes a first slot 614 extending from a perimeter of the first electrode 610 to an interior of the first electrode 610. In an example, the first electrode 610 can be used as an anode layer of a capacitor, such as, for instance, a capacitor of an IMD. In some examples, a segmented second electrode 620 can be separated from the first electrode 610 by a first distance, as shown in FIG. 8. In an example, the second electrode 620 can include a second slot 624 extending from a perimeter of the second electrode 620 to an interior of the second electrode 620. In an example, the second electrode 620 can be used as a cathode layer of a capacitor, such as, for instance, a capacitor of an IMD. In an example, the first and second slots 614, 624 can be configured to at least partially segment surface areas of the first and second electrodes 610, 620, respectively, to reduce a radial current loop size in each of the first and second electrodes 610, 620, in a manner similar to that described above with respect to the example electrode 310. In an example, one or more pairs of first and second electrodes 610, 620 can be stacked (as seen generally in FIG. 8) to form a capacitor. In a further example, the capacitor can be an AE capacitor, as described above, in which the first electrode 610 includes an aluminum substrate at least partially covered with aluminum oxide. In a still further example, the capacitor can be an AE capacitor, as described above, in which the second electrode 620 includes an aluminum substrate at least partially covered with sputtered titanium.

In another example, the first electrode 610 can be substantially parallel to the second electrode 620 in a stacked configuration, as generally shown in FIG. 8. In an example, a separator can be disposed between the first electrode 610 and the second electrode 620. In a further example, the separator can include capacitor paper. In another example, the separator can include an electrolyte material.

In an example, the first and second slots 614, 624 are generally aligned with one another with the first and second electrodes 610, 620 in the stacked configuration. In a further example, the first and second slots 614, 624 can be disposed substantially along a center of the first and second electrodes 610, 620, respectively. In another example, the first slot 614 can be offset from the second slot 624 with the first and second electrodes 610, 620 in the stacked configuration. That is, the first and second slots 614, 624 can be staggered so as not to be one on top of the other with the first and second electrodes 610, 620 in the stacked configuration. In an example, such an offset configuration can reduce the amount of large void volumes in which electrolyte can potentially pool in the capacitor, which can potentially lead decreased performance of the capacitor. In another example, such an offset configuration can inhibit the possibility of shorting between anode and cathode layers, for instance by decreasing the likelihood of a contaminant or other object becoming positioned across and remaining in contact with each of at least one anode and one cathode. In the example including the aligned slot configuration described above, the alignment of the first and second slots 614, 624 can provide an area for a contaminant or other object to become lodged or otherwise positioned in contact with and across each of at least one anode and one cathode. However, if, in some instances, such a configuration is considered desirable, the possibility of such contaminants shorting the capacitor can be reduced with added care during manufacturing of the capacitor.

In an example, the first electrode 610 can include a first interconnection area 616 substantially centrally located along an edge of the first electrode 610 and substantially proximate an end of the first slot 614 that is disposed in the interior of the first electrode 610. That is, the first interconnection area 616 can be located proximate the area of the first electrode 610 having a reduced cross section, in a manner similar to that described with respect to the example above including the interconnection area 516. In a further example, the second electrode 620 can include a second interconnection area 626 substantially centrally located along an edge of the second electrode 620 and substantially proximate an end of the second slot 624 that is disposed in the interior of the second electrode 620. That is, the second interconnection area 626 can be located proximate the area of the second electrode 620 having a reduced cross section, in a manner similar to that described with respect to the example above including the interconnection area 516. Such interconnection areas 616, 626 allow for two or more first electrodes 610 (for instance, anode layers) to be connected using a connection member and for two or more second electrodes 620 (for instance, cathode layers) to be connected using another connection member. By positioning the first and second interconnection areas 616, 626 at or proximate the reduced cross sections of the segmented first and second electrodes 610, 620, increases in ESR and other detrimental performance effects of the capacitor due to the reduced cross section of the first and second electrodes 610, 620 can be reduced, in a manner similar to that described with respect to the example electrode 510 above.

In a further example, the first interconnection area 616 can be offset from the second interconnection area 626 to allow for interconnection of two or more first electrodes 610 and for interconnection of two or more second electrodes 620 without having the first interconnection area 616 interfering or otherwise getting in the way of the second interconnection area 626 with the first and second electrodes 610, 620 in the stacked configuration. Simply put, in an example, the first and second interconnection areas 616, 626 cannot occupy the same area without increased manufacturing complexities.

In an effort to simplify manufacturing of the capacitor, in an example, the first interconnection area 616 of the first electrode 610 can be positioned slightly to one side of a center of the first electrode 610 and the second interconnection area 626 of the second electrode 620 can be positioned slightly to the other side of a center (aligned with the center of the first electrode 610 with the first and second electrodes 610, 620 in the stacked configuration) of the second electrode 620. In this way, two or more first electrodes 610 can be interconnected without interfering with the interconnection of two or more second electrodes 620. In further examples, the first electrode 610 can include a cutout 618 configured to align with the second interconnection area 626 of the second electrode 620, with the first and second electrodes 610, 620 in the stacked configuration, wherein the cutout 618 can allow for a connection member from one second electrode 620 to another second electrode 620 to pass by the first electrode 610 without contacting the first electrode 610. In this way, the cutout 618 reduces shorting concerns associated with interconnecting second electrodes 620. In other examples, the second electrode 620 can include a cutout 628 configured to align with the first interconnection area 616 of the first electrode 610, with the first and second electrodes 610, 620 in the stacked configuration, to reduce shorting concerns associated with interconnecting first electrodes 610 in a manner similar to that described about with respect to the cutout 618.

Figure 9:
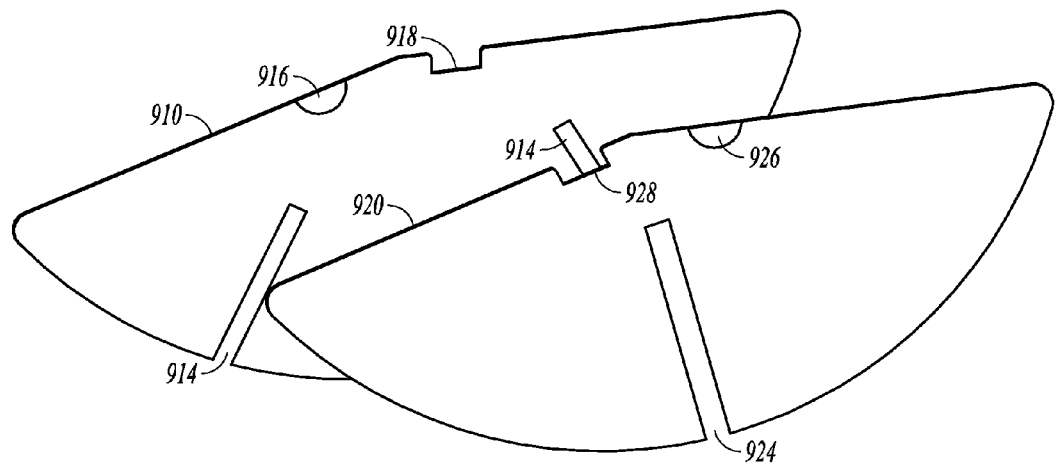
FIG. 9 illustrates an example of segmented electrodes including interconnect areas, the segmented electrodes including substantially offset segmentations.
Figure 10:
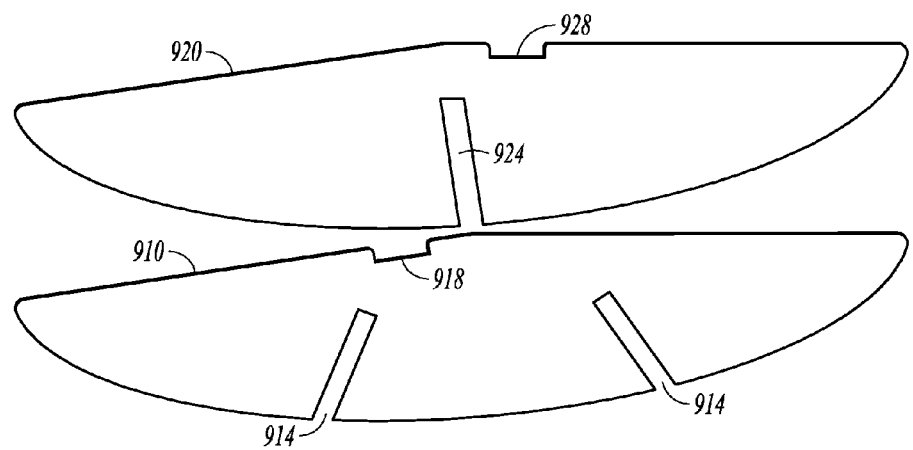
FIG. 10 illustrates an example of segmented electrodes including interconnect areas, the segmented electrodes including substantially offset segmentations.

With reference to FIGS. 9 and 10, in some examples, segmented first and second electrodes 910, 920 are shown generally in a stacked configuration. In various examples, such first and second electrodes 910, 920 can be used in a capacitor for an IMD. In an example, the segmented first electrode 910 includes two first slots 914 each extending from a perimeter of the first electrode 910 to an interior of the first electrode 910. In an example, the first electrode 910 can be used as an anode layer of a capacitor, such as, for instance, a capacitor of an IMD. In an example, the segmented second electrode 920 can include a second slot 924 extending from a perimeter of the second electrode 920 to an interior of the second electrode 920. In an example, the second electrode 920 can be used as a cathode layer of a capacitor, such as, for instance, a capacitor of an IMD. In an example, the first and second slots 914, 924 can be configured to at least partially segment surface areas of the first and second electrodes 910, 920, respectively, to reduce a radial current loop size in each of the first and second electrodes 910, 920, in a manner similar to that described in the examples above with respect to the first and second electrodes 610, 620.

The first electrode 910 can include the two first slots 914 for various reasons. In an example, a thickness of the first electrode 910 can be large enough that increased segmenting of the first electrode 910 is desirable to sufficiently reduce the loop size of the eddy currents in the first electrode 910 to reduce the heating and/or movement induced by an MRI environment to a level at which the first electrode 910 is deemed MRI Safe. For instance, in an example, the thickness of the first electrode 910 can be approximately four times the thickness of the second electrode 920. In another example, the two first slots 914 can allow for each of the first slots 914 to be offset from the second slot 924 with the first and second electrodes 910, 920 in the stacked configuration. That is, the first and second slots 914, 924 can be staggered so as not to be one on top of the other with the first and second electrodes 910, 920 in the stacked configuration. In an example, such an offset configuration can reduce the amount of large void volumes in which electrolyte can potentially pool in the capacitor, which can potentially lead decreased performance of the capacitor. In another example, such an offset configuration can inhibit the possibility of shorting between anode and cathode layers, for instance by decreasing the likelihood of a contaminant or other object becoming positioned across and remaining in contact with each of at least one anode and one cathode. In the example including the aligned slot configuration described above, the alignment of the first and second slots 914, 924 can provide an area for a contaminant or other object to become lodged or otherwise positioned in contact with and across each of at least one anode and one cathode.

In an example, the first electrode 910 can include a first interconnection area 916 located along an edge of the first electrode 910 and substantially equidistant from an interiorly-disposed end of each of the first slots 914. In this way, the first interconnection area 916 can be located proximate each area of the first electrode 910 having a reduced cross section. In a further example, the second electrode 920 can include a second interconnection area 926 substantially centrally located along an edge of the second electrode 920 and substantially proximate an end of the second slot 924 that is disposed in the interior of the second electrode 920. That is, the second interconnection area 926 can be located proximate the area of the second electrode 920 having a reduced cross section. Such interconnection areas 916, 926 allow for two or more first electrodes 910 (for instance, anode layers) to be connected using a connection member and for two or more second electrodes 920 (for instance, cathode layers) to be connected using another connection member. By positioning the first and second interconnection areas 916, 926 at or proximate the reduced cross sections of the segmented first and second electrodes 910, 920, increases in ESR and other detrimental performance effects of the capacitor due to the reduced cross section of the first and second electrodes 910, 920 can be reduced, in a manner similar to that described with respect to the example electrode 510 above.

In an example, the first interconnection area 916 can be positioned slightly to one side of a center of the first electrode 910, and the second interconnection area 926 can be positioned slightly to the other side of a center (aligned with the center of the first electrode 910 with the first and second electrodes 910, 920 in the stacked configuration) of the second electrode 920. In this way, two or more first electrodes 910 can be interconnected without interfering with the interconnection of two or more second electrodes 920. In further examples, the first electrode 910 can include a cutout 918 configured to align with the second interconnection area 926 of the second electrode 920, with the first and second electrodes 910, 920 in the stacked configuration, wherein the cutout 918 can allow for a connection member from one second electrode 920 to another second electrode 920 to pass by the first electrode 910 without contacting the first electrode 910. In this way, the cutout 918 reduces shorting concerns associated with interconnecting second electrodes 920. In other examples, the second electrode 920 can include a cutout 928 configured to align with the first interconnection area 916 of the first electrode 910, with the first and second electrodes 910, 920 in the stacked configuration, to reduce shorting concerns associated with interconnecting first electrodes 910 in a manner similar to that described about with respect to the cutout 918.

In an example, a method can include stacking a first electrode with a second electrode, wherein the second electrode is separated from the first electrode by a first distance. In an example, the method can include placing a separator in between the first and second electrodes. In an example, the separator includes capacitor paper. In a further example, the separator includes an electrolyte. The first electrode can include a first slot extending through the first electrode from a perimeter of the first electrode to an interior of the first electrode. The second electrode can include a second slot extending through the second electrode from a perimeter of the second electrode to an interior of the second electrode.

The first and second slots can be configured to at least partially segment a surface area of the first and second electrodes, respectively, to reduce a radial current loop size in each of the first and second electrodes. The method, in some examples, can include segmenting the first and second electrodes to form the first and second slots. In a further example, the first electrode is segmented to form more than one first slot.

With reference to the examples described above, various manufacturing operations are contemplated for producing the segmented electrodes. In an example, segmenting of the first and second electrodes includes die cutting the first and second electrodes to form the first and second slots. In a further example, die cutting can be used to cut the electrodes to the desired size and shape, while, at the same time, forming the one of more openings or slots in the electrode. With respect to AE capacitors, as described above, an anode layer can include aluminum oxide, which can be relatively brittle. However, the present inventors have recognized that die cutting of such a brittle material can be performed with at least an adequate success rate.

The above described examples illustrate segmented components of an IMD and methods of making such segmented IMD components, with such segmented components including a reduced response (as compared to un-segmented components) to magnetic fields present in an MRI environment. In some examples, such segmentation can be included in IMD capacitors. In further examples, electrodes, including anodes and/or cathodes, of IMD capacitors can be segmented in order to make the IMD capacitor MRI Safe. By segmenting IMD components as described above, the present inventors have recognized that eddy currents in the IMD components can be reduced, thereby resulting in reduced heating and/or vibration of the segmented components when exposed to an MRI environment. In this way, examples of the segmented IMD components and methods, such as those described above, can be used in various IMDs to make such IMDs MRI Safe.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An implantable medical device capacitor comprising:
   a first electrode including:
      a first slot extending from a perimeter of the first electrode to an interior of the first electrode; and
      a first interconnection area substantially centrally located along an edge of the first electrode and substantially proximate an end of the first slot, the end being disposed in the interior of the first electrode; and
   a second electrode separated from the first electrode by a first distance, the second electrode including:
      a second slot extending from a perimeter of the second electrode to an interior of the second electrode; and
      a second interconnection area substantially centrally located along an edge of the second electrode and substantially proximate an end of the second slot, the end being disposed in the interior of the second electrode;
   wherein the first and second slots are configured to at least partially segment surface areas of the first and second electrodes, respectively, to reduce a radial current loop size in each of the first and second electrodes.

2. The implantable medical device capacitor of claim 1, wherein the first electrode includes an anode layer.

3. The implantable medical device capacitor of claim 1, wherein the second electrode includes a cathode layer.

4. The implantable medical device capacitor of claim 1, wherein the first electrode includes an aluminum substrate at least partially covered with aluminum oxide.

5. The implantable medical device capacitor of claim 1, wherein the second electrode includes an aluminum substrate at least partially covered with sputtered titanium.

6. The implantable medical device capacitor of claim 1, wherein the first electrode is substantially parallel to the second electrode in a stacked configuration.

7. The implantable medical device capacitor of claim 6, wherein the first slot of the first electrode is substantially aligned with the second slot of the second electrode.

8. The implantable medical device capacitor of claim 6, wherein the first slot of the first electrode is offset from the second slot of the second electrode.

9. The implantable medical device capacitor of claim 6, comprising a separator disposed between the first electrode and the second electrode.

10. The implantable medical device capacitor of claim 9, wherein the separator includes an electrolyte material.

11. The implantable medical device capacitor of claim 1, wherein the first electrode includes more than one first slot.

12. The implantable medical device capacitor of claim 1, wherein the first and second electrodes are substantially planar.

13. The implantable medical device capacitor of claim 1, wherein the first interconnection area of the first electrode is offset from the second interconnection area of the second electrode with the first and second electrodes in a stacked configuration.

14. The implantable medical device capacitor of claim 1, wherein the first electrode includes two first slots, the first interconnection area being located along the edge of the first electrode and substantially equidistant from an end of each of the first slots, the ends disposed in the interior of the first electrode.

15. A method comprising:
stacking a first electrode with a second electrode, wherein the second electrode is separated from the first electrode by a first distance, the first electrode including a first slot extending through the first electrode from a perimeter of the first electrode to an interior of the first electrode, the first electrode including a first interconnection area substantially centrally located along an edge of the first electrode and substantially proximate an end of the first slot, the end being disposed in the interior of the first electrode, the second electrode including a second slot extending through the second electrode from a perimeter of the second electrode to an interior of the second electrode, the second electrode including a second interconnection area substantially centrally located along an edge of the second electrode and substantially proximate an end of the second slot, the end being disposed in the interior of the second electrode, wherein the first and second slots are configured to at least partially segment a surface area of the first and second electrodes, respectively, to reduce a radial current loop size in each of the first and second electrodes.

16. The method of claim 15, comprising segmenting the first and second electrodes to form the first and second slots.

17. The method of claim 16, wherein segmenting includes segmenting the first electrode to form more than one first slot.

18. The method of claim 15, wherein segmenting includes die cutting the first and second electrodes to form the first and second slots.

19. The method of claim 15, comprising placing a separator in between the first and second electrodes.

\* \* \* \* \*